(12) United States Patent
Tu et al.

(10) Patent No.: US 9,109,003 B2
(45) Date of Patent: Aug. 18, 2015

(54) **EXTRACTION METHOD FOR *ILEX KUDINGCHA* C. J. TSENG LEAVES, TOTAL SAPONINS AND USE THEREOF**

(75) Inventors: Pengfei Tu, Beijing (CN); Tongmei Zhang, Beijing (CN); Jiao Zheng, Beijing (CN); Yong Jiang, Beijing (CN); Haiyan Zhou, Beijing (CN); Li Tang, Beijing (CN); Zhizhong Ma, Beijing (CN)

(73) Assignee: Peking University, Beijing (CN)

( * ) Notice: Subject to any disclaimer, the term of this patent is extended or adjusted under 35 U.S.C. 154(b) by 86 days.

(21) Appl. No.: 13/981,054

(22) PCT Filed: Dec. 21, 2011

(86) PCT No.: PCT/CN2011/084377
§ 371 (c)(1),
(2), (4) Date: Jul. 22, 2013

(87) PCT Pub. No.: WO2012/100612
PCT Pub. Date: Aug. 2, 2012

(65) Prior Publication Data
US 2013/0303469 A1 Nov. 14, 2013

(30) Foreign Application Priority Data
Jan. 24, 2011 (CN) .......................... 2011 1 0026026

(51) Int. Cl.
*C07H 15/256* (2006.01)
*A61K 31/704* (2006.01)
*A61K 36/185* (2006.01)

(52) U.S. Cl.
CPC ............ *C07H 15/256* (2013.01); *A61K 31/704* (2013.01); *A61K 36/185* (2013.01); *A61K 2236/333* (2013.01)

(58) Field of Classification Search
CPC ......................... C07H 15/256; A61K 31/704
USPC ...................... 514/25; 536/6.1, 6.3
See application file for complete search history.

(56) References Cited

U.S. PATENT DOCUMENTS

2008/0234208 A1 * 9/2008 Sun et al. ................ 514/26

OTHER PUBLICATIONS

Zheng et al. Improving abnormal hemorheological parameters in ApoE-/- mice by *Ilex kudingcha* total saponins. Clin Hemorheol Microcirc 42:29-36, 2009.*
Tang et al. Triterpene Saponins from the Leaves of *Ilex kudingcha*. J Nat Prod 68:1169-1174, 2005.*
English Translation of claims 3-7 and paragraph 3, p. 1 of the description of CN 101361766 A (2 pages), Feb. 2009.
English Abstract of CN 101766664 A (1 page), Jul. 2010.
English Abstract of CN 1521175 A (1 page), Aug. 2004.
English Abstract of CN 1981803 A (1 page), Jun. 2007.
English Abstract of CN 101284031 A (1 page), Oct. 2008.
International Search Report of corresponding Application No. PCT/CN2011/084377, dated Mar. 15, 2012, with English Translation (10 pages).
"Total saponins from Kuding tea (*Ilex kudingcha* C. J. Tseng) protect against kidney injury induced by hypercholesterolemia in apolipoprotein E knockout mice," Chinese Journal of New Drugs, vol. 18, No. 5, Dec. 31, 2009, p. 430, lines 1-7, and p. 429, abstract, line 4.

* cited by examiner

*Primary Examiner* — Mark Shibuya
*Assistant Examiner* — Yih-Horng Shiao
(74) *Attorney, Agent, or Firm* — Christie, Parker & Hale, LLP

(57) ABSTRACT

The present invention provides an extraction method for the leaves of *Ilex kudingcha* C. J. Tseng, and the total saponins from *I. kudingcha* leaves extracted by using this method, and use of the total saponins in preparing a drug for reducing cholesterol and blood lipids and anti-atherosclerosis. The extraction method comprises the following steps: subjecting *I. kudingcha* leaves to refluxing extraction with ethanol aqueous solution to obtain an extracted solution; filtering the extracted solution and removing ethanol, and then separating and purifying the solution using a macroporous resin column.

18 Claims, 7 Drawing Sheets

US 9,109,003 B2

EXTRACTION METHOD FOR *ILEX KUDINGCHA* C. J. TSENG LEAVES, TOTAL SAPONINS AND USE THEREOF

CROSS-REFERENCE TO RELATED APPLICATION(S)

This application is a National Phase Patent Application and claims priority to and benefit of International Application Number PCT/CN2011/084377, filed on Dec. 21, 2011, which claims priority to and benefit of Chinese Patent Application Number 201110026026.X, filed on Jan. 24, 2011, the entire disclosures of which are incorporated herein by reference.

TECHNICAL FIELD

This present invention relates to an extraction method for *Ilex kudingcha* C. J. Tseng leaves, and the total saponins from *I. kudingcha* leaves extracted by using this method and use thereof. Specifically, the present invention pertains to a method for extracting total saponins from *I. kudingcha* leaves, and the total saponins extracted by this method can be used for reducing cholesterol and blood lipids and anti-atherosclerosis.

BACKGROUND

Hyperlipidemia includes high cholesterol and high triglycerides, wherein the harmfulness of the former is far greater than that of the latter. As for hyperlipidemia, the drug-induced lipid-lowering therapy is the most effective measure for the treatment of hyperlipidemia. At present, although there have been many effective drugs for reducing triglycerides, the drugs for reducing cholesterol are mainly statins. These statins drugs are mainly for resisting hypercholesterolemia-induced atherosclerosis, and the action mechanism of these drugs is inhibiting the synthesis of hepatic cholesterol. However, long-term use of statins has apparent toxic effects on the liver and muscle, and also leads to increase of transaminases, even a few patients suffer rhabdomyolysis and acute renal failure. The problem of toxicity and side effects of statins has not yet been solved, even after several generations of drug structure modification.

*Kudingcha* is a traditional folk beverage, which has been drinking for nearly a thousand years as a healthy tea, with functions such as losing weight, reducing blood lipids and blood pressure and anti-fever and detoxicity. There are various *Kudingcha* in the market, which are made from the leaves of 22 kinds of different plants according to the surveys. But which kind of *Kudingcha* has better effects on reducing blood lipids and blood pressure is unknown, resulting in spending too much money by consumers, but with minimal lipid-lowering effect, even no effect.

SUMMARY

In recent years, the inventors of the present invention have found that only the leaves of the *Ilex kudingcha* C. J. Tseng, the plant of genus *Ilex* have very distinct effects of reducing blood lipids and anti-atherosclerosis after systematic comparative studies, wherein the active ingredients are saponins, and the aglycones of saponins from *I. kudingcha* are significantly different from those from other *Kudingcha* varieties. After systematic study on active ingredients and pharmacological effects, the inventors have found that saponins from *I. kudingcha* have a significant effect on reducing cholesterol and anti-atherosclerosis, which is equivalent to the effect of statin drugs, but the mechanism of saponins from *I. kudingcha* is completely different from that of statin drugs. In addition, such saponins also have functions, such as reducing triglycerides, resisting oxidation, protecting kidney, and improving blood rheology. Study on the action mechanism has shown that the mechanism of reducing lipids by saponins from *I. kudingcha* is through inhibiting the activity of the acyl-coenzyme A cholesterol acyl transferase (ACAT) in intestinal tract and liver, so that the intestinal absorption of cholesterol can be inhibited. However, the content of isochlorogenic acids is much higher than that of saponins in the extract of *I. kudingcha* extracted by the conventional extraction methods. Furthermore, the inventors also found that the isochlorogenic acids could increase the blood lipids.

Therefore, one object of the present invention is to provide an extraction method for *I. kudingcha* leaves, which can separate the total saponins and the total isochlorogenic acids, so that the extract containing high content of saponins and the extract containing high content of total isochlorogenic acids can be obtained respectively; another object of the present invention is to provide the total saponins of *I. kudingcha* leaves extracted by using the method of the present invention, which contain more than 80% saponins, and can be used for reducing blood lipids, anti-atherosclerosis, and protecting the liver and kidney; and the third object of the present invention is to provide use of the above total saponins in preparing a drug for reducing cholesterol and blood lipids and anti-atherosclerosis.

For the objects of the invention described above, the present invention provides the following technical solutions.

The present invention provides an extraction method for the leaves of *I. kudingcha*, including the following steps: (1) subjecting *I. kudingcha* leaves to refluxing extraction with 50~70% ethanol aqueous solution to obtain an extract solution; (2) filtering the extract solution and removing ethanol from the extract solution; (3) adsorbing the solution obtained in step (2) by macroporous resin column, and eluting the resin column with $H_2O$, 10~30% alkaline ethanol aqueous solution (pH 9~11), 10~30% ethanol aqueous solution and 50%~70% ethanol aqueous solution, successively; (4) collecting, concentrating and drying the eluate of 50~70% ethanol aqueous solution to obtain an extract of *I. kudingcha* leaves.

In the extraction method of the present invention, the concentration of the ethanol aqueous solution in step (1) may be preferably 55~65%, most preferably 60%; and the concentration of the ethanol aqueous solution in step (3) may be preferably 55~65%, most preferably 60%. In the present invention, the concentration of the ethanol aqueous solution refers to the volume percentage of ethanol in the ethanol aqueous solution.

In the extraction method of the present invention, the operation of refluxing extraction in step (1) is known to those skilled in the art, and the amount of the ethanol aqueous solution in the operation can be determined according to the amounts of raw materials. For example, the weight ratio of the ethanol aqueous solution and the raw materials may be 2~20:1, preferably 5~15:1. Extraction times may be 1~8 times, preferably 2~4 times; time for each refluxing extraction may be 0.5~5 h, preferably 0.5~2 h. Time for each refluxing extraction may be the same or different, and the concentration of the ethanol aqueous solution for each refluxing extraction may be the same or different, and also the amount of ethanol aqueous solution for each refluxing extraction may be the same or different. For example, in a preferred embodiment of the present invention, 60% ethanol in an amount of 10 times the weight of the raw materials is used for refluxing for 1 h first; after filtration, the materials are refluxed for 1 hour with 60% ethanol in an amount of 8 times the weight of the raw materials; and then refluxed for 1 hour with 60% ethanol in an amount of 8 times the weight of raw materials after been filtered, and filtrates obtained by three refluxing extractions are combined.

In the extraction method of the present invention, the method for removing the ethanol in step (2) and the method for concentrating the eluent in step (4) are known to those skilled in the art. For example, the two methods may be both concentrated under reduced pressure. The method for drying in step (4) is preferably vacuum drying. In order to save the amount of ethanol, the method of the present invention may further includes: ethanol separated in step (2) and/or ethanol separated in step (4) are recovered to be used again in refluxing extraction in step (1).

In the extraction method of the present invention, the macroporous resin column used in step (3) is the resin column used commonly in the art. In the present invention, the styrene-type macroporous adsorptive resins, such as D101, HPD100, HPD400A, AB-8 and NKA are preferred. The ratio of diameter to height of the macroporous resin column may be 1:3~10, preferably 1:4~7 and most preferably 1:6. The weight ratio of the resin and *I. kudingcha* leaves may be 5~15:1, preferably 6~10:1, and most preferably 7:1.

Preferably, in order to obtain the total saponin extract with high potency, the elution process in step (3) may include: eluting the resin column with 4~10 column volumes of water until there is no saccharides, and then eluting the resin column with 5~10 column volumes of 10~30% alkaline ethanol aqueous solution (pH 9~11); and then eluting the resin column with 2~5 column volumes of 10~30% ethanol aqueous solution; finally, eluting the resin column with 3~6 column volumes of 50~70% ethanol aqueous solution. For example, in a preferred embodiment of the present invention, the step (3) includes: adsorbing the solution obtained in step (2) statically by HPD400A macroporous resin column (the ratio of diameter to height of the resin column is 1:4 and the weight ratio of the resin and herb is 7:1) for 30 minutes, repeating the above process three times; after adsorption, eluting the resin column with water until there is no saccharide, and then eluting the resin column with 8 column volumes of 25% alkaline ethanol aqueous solution (pH=10); and then eluting the resin column with 3 column volumes of 25% neutral ethanol aqueous solution until the resin column is neutral; finally, eluting the resin column with 4 column volumes of 60% ethanol aqueous solution; collecting, concentrating and drying the eluent of 60% ethanol aqueous solution to obtain the extract of total saponins of *I. kudingcha* leaves.

In the extraction method of the present invention, the pH of the alkaline ethanol aqueous solution in step (3) is most preferably 10.

The method of the present invention may further include step (5): combining the eluate of 10~30% alkaline ethanol aqueous solution (pH 9~11) and the eluate of 10~30% ethanol aqueous solution, adjusting the pH of the combined solution to pH 2~3, and then concentrating the solution and drying to obtain the total isochlorogenic acids.

The present invention also provides the total saponins from *I. kudingcha* leaves extracted by using the above method, in which the content of total saponins can reach above 80%. The total saponins of the present invention can reduce blood lipids and resist atherosclerosis, and also have a protective effect on the liver and kidney.

The present invention also provides use of total saponins from *I. kudingcha* leaves extracted by using the above method in preparing a drug for reducing cholesterol and blood lipids and resisting atherosclerosis. The total saponins from *I. kud-ingcha* leaves can either be used alone, or used in combination with statin drugs to enhance the efficacy and reduce the toxic and side effects of statin drugs.

The present invention also provides a method for reducing cholesterol and blood lipids and anti-atherosclerosis by using the total saponins from *I. kudingcha* leaves provided in the present invention.

The total saponins from *I. kudingcha* leaves provided by the present invention have a significant effect on reducing cholesterol and anti-atherosclerosis, which is equivalent to the effect of statin drugs, but the mechanism of saponins from *I. kudingcha* is completely different from that of statin drugs. In addition, the extract of total saponins in the present invention also has such functions as reducing triglycerides, resisting oxidation, protecting kidney, and improving blood rheology. Studies on the action mechanism showed that the mechanism of reducing blood lipids by saponins from *I. kudingcha* leaves is as follows: saponins from *I. kudingcha* leaves can inhibit the activity of acyl-coenzyme A cholesterol acyl transferase (ACAT) in intestinal tract and liver, thereby the absorption of cholesterol in intestinal tract can be inhibited.

BRIEF DESCRIPTION OF THE DRAWINGS

Hereinafter, the embodiments of the present invention will be described in detail with reference to the accompanying drawings, in which.

DETAILED DESCRIPTION OF PREFERRED EMBODIMENTS

Figure 1:
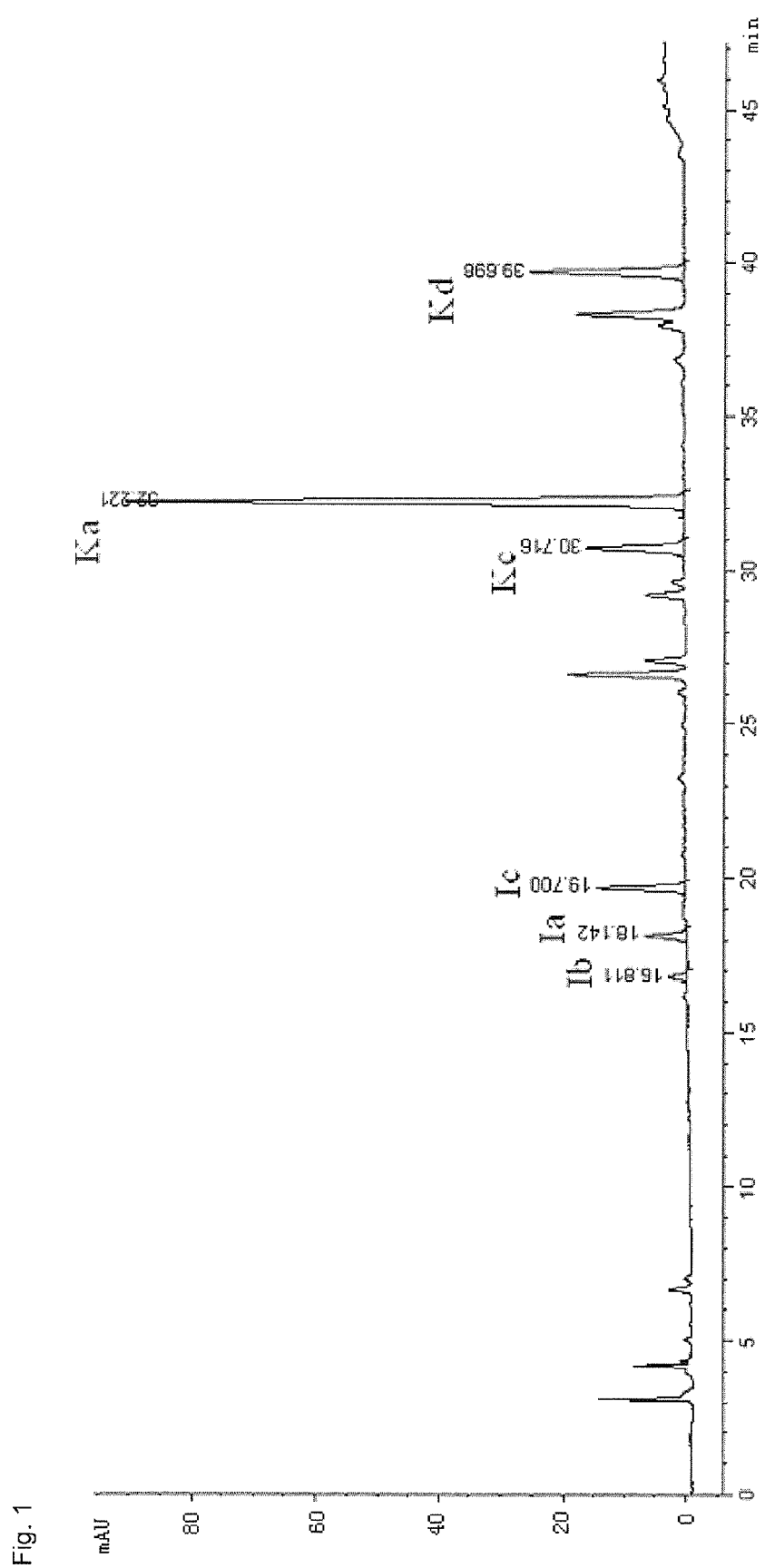
FIG. 1 is a high performance liquid chromatogram of sample A1 prepared in Example 1.

The present invention will be further illustrated in combination with specific embodiments. However, these embodiments are only used to illustrate the present invention, rather than to limit the scope of the present invention. It should be noted that ethanol of various percentage concentrations mentioned in the embodiments refers to the ethanol aqueous solutions of corresponding volume percentage concentrations.

Example 1

This example is used to illustrate the extraction method for *I. kudingcha* leaves provided in the present invention.

Extraction: 0.5 kg medical material of *I. kudingcha* was weighed, then refluxing extraction was performed respectively with 5 L 60% ethanol for 0.5 h and with 4 L 60% ethanol for 1 h, and the filtrates were combined after filtration;

Removing ethanol: the extracted filtrate was concentrated under reduced pressure until there was no alcohol taste, so that ethanol was recovered, wherein the relative density of the concentrated solution was 1.06~1.08 (at room temperature);

Adsorption: the concentrated solution was applied to a HPD400A macroporous resin column, and the eluent was reloaded on the resin column for 3 times, wherein the resin column was filled with 5 kg resins, and the ratio of diameter to height of the resin column is 1:4, and the loaded column was keeping statically for 30 min.

Washing impurity: the resin column was eluted with 4 column volumes of deionized water until there were no saccharides, and then eluted with 8 column volumes of 20% alkaline ethanol (NaOH, pH=10), and then eluted with 3 column volumes of 20% ethanol until neutral.

Elution: the extract adsorbed in the resin was further eluted with 6 column volumes of 60% ethanol.

Concentration and drying: the eluate was concentrated under reduced pressure to recover ethanol, then dried in vacuum. The dried solid was grinded and sifted through 100-mesh screen, and 65.35 g extract of *I. kudingcha* leaves was obtained, which was marked as A1, and the extraction yield was 13.07%.

Example 2

This example is used to illustrate the extraction method for *I. kudingcha* leaves provided in the present invention.

Extraction: 0.5 kg medical material of *I. kudingcha* was weighed, then refluxing extraction was performed respectively with 4 L 65% ethanol for 2 h, with 3 L 60% ethanol for 1 h and with 3 L 50% ethanol for 0.5 h, successively, and the filtrates were combined after filtration.

Removing ethanol: the extracted filtrate was concentrated under reduced pressure until there was no alcohol taste, so that the ethanol was recovered, wherein the relative density of concentrated solution was 1.06~1.08 (at room temperature);

Adsorption: the concentrated solution was subjected to an AB-8 macroporous resin column, wherein the resin column was filled with 3.5 kg resin, and the ratio of diameter to height of the resin column is 1:8;

Washing impurity: the resin column was eluted with 8 column volumes of deionized water until there were no saccharides, and then eluted with 10 column volumes of 30% alkaline ethanol (NaOH, pH=10.5), and then eluted with 4 column volumes of 30% ethanol until neutral;

Elution: the extract adsorbed in the resin was further eluted with 3 column volumes of 65% ethanol;

Concentration and drying: the eluate was concentrated under reduced pressure, then dried in vacuum, the dried solid was grinded and sifted through 100-mesh screen, and 50.31 g extract of *I. kudingcha* leaves was obtained, which was marked as A2, and the extraction yield was 10.06%.

Comparative Example 1

This comparative example is used to illustrate the extraction method for *I. kudingcha* leaves, in which only water was used to perform elution in the step of washing impurity.

Processes of extraction, removing ethanol and adsorption were performed by using the same method as Example 1;

Washing impurity: the resin column was eluted with 4 column volumes of deionized water until there were no saccharides;

Elution: the extract adsorbed in the resin was further eluted with 4 column volumes of 60% ethanol;

Concentration and drying: the eluate was concentrated under reduced pressure, then dried in vacuum, and the dried solid was grinded and sifted through 100-mesh screen, to obtain 150 g extract of *I. kudingcha* leaves, which was marked as C1, and the extraction yield was 30.00%.

Comparative Example 2

This comparative example is used to illustrate the extraction method for *I. kudingcha* leaves, in which only water and ethanol were used to perform elution in the step of washing impurity.

Processes of extraction, removing ethanol and adsorption were performed according to the same method as Example 1;

Washing impurity: the resin column was eluted with 4 column volumes of deionized water until there were no saccharides, and then eluted with 5 column volumes of 10% ethanol;

Elution: the extract adsorbed in the resin was further eluted with 4 column volumes of 60% ethanol;

Concentration and drying: the eluate was concentrated under reduced pressure, then dried in vacuum, and the dried solid was grinded and sifted through 100-mesh screen, to obtain 110.23 g extract of *I. kudingcha* leaves, which was marked as C2, and the extraction yield was 22.05%.

Comparative Example 3

This comparative example is used to illustrate the extraction method for *I. kudingcha* leaves, in which only water and ethanol were used to perform elution in the step of washing impurity.

Processes of extraction, removing ethanol and adsorption were performed according to the same method as Example 1;

Washing impurity: the resin column was eluted with 4 column volumes of deionized water until there were no saccharides, and then eluted with 11 column volumes of 20% ethanol;

Elution: the extract adsorbed in the resin was further eluted with 4 column volumes of 60% ethanol;

Concentration and drying: the eluent was concentrated under reduced pressure, then dried in vacuum, and the dried solid was grinded and sifted through 100-mesh screen, to obtain 102.8 g extract of *I. kudingcha* leaves, which was marked as C3, and the extraction yield was 20.56%.

Determination of Ingredients

1. Detection by High Performance Liquid Chromatography (HPLC)

Chromatographic column: Kromasil C18 (4.6×250 mm, 5 μm);

Flow rate: 0.8 ml/min;

Detection wavelength: 226 nm;

Column temperature: 30° C.;

Mobile phase: acetonitrile—0.1% phosphoric acid solution, gradient elution;

Conditions for elution were shown in Table 1:

TABLE 1

| Conditions for gradient elution | |
|---|---|
| Time/min | Acetonitrile/% |
| 0~12 | 15~23 |
| 12~20 | 23~30 |
| 20~40 | 30~40 |
| 40~50 | 40~95 |

Figure 2:
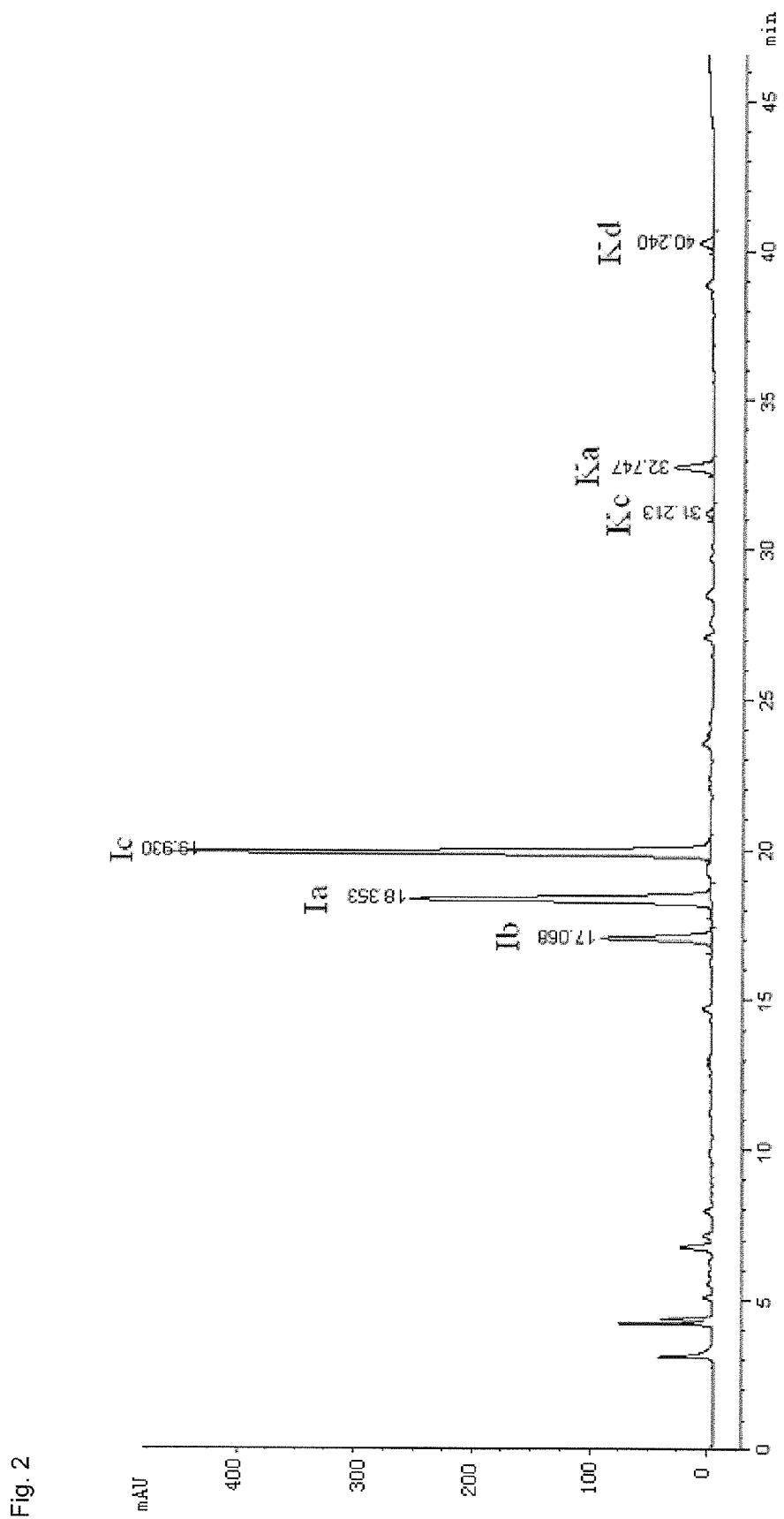
FIG. 2 is a high performance liquid chromatogram of sample C1 prepared in Comparative Example 1.
Figure 3:
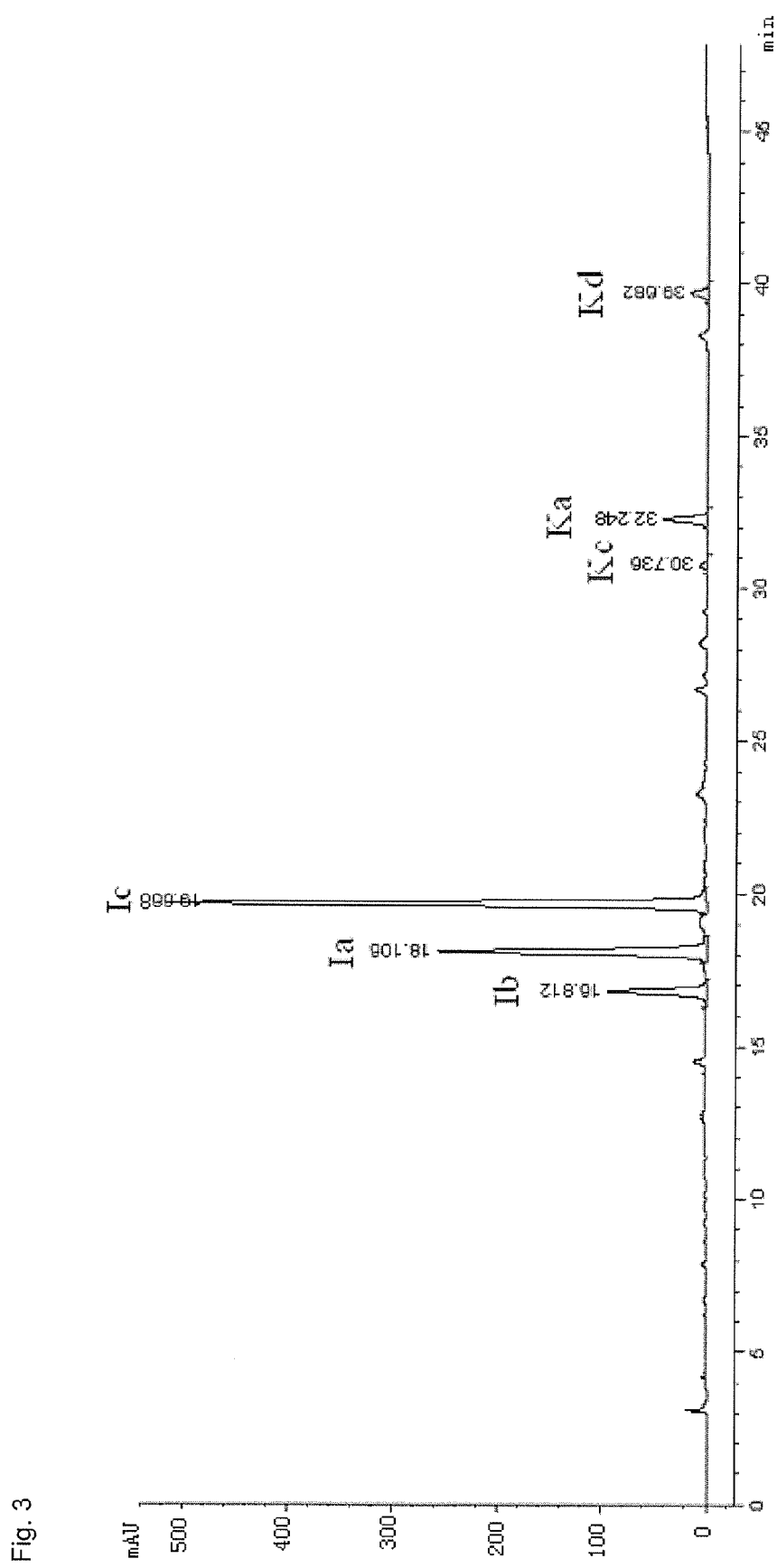
FIG. 3 is a high performance liquid chromatogram of sample C2 prepared in Comparative Example 2.
Figure 4:
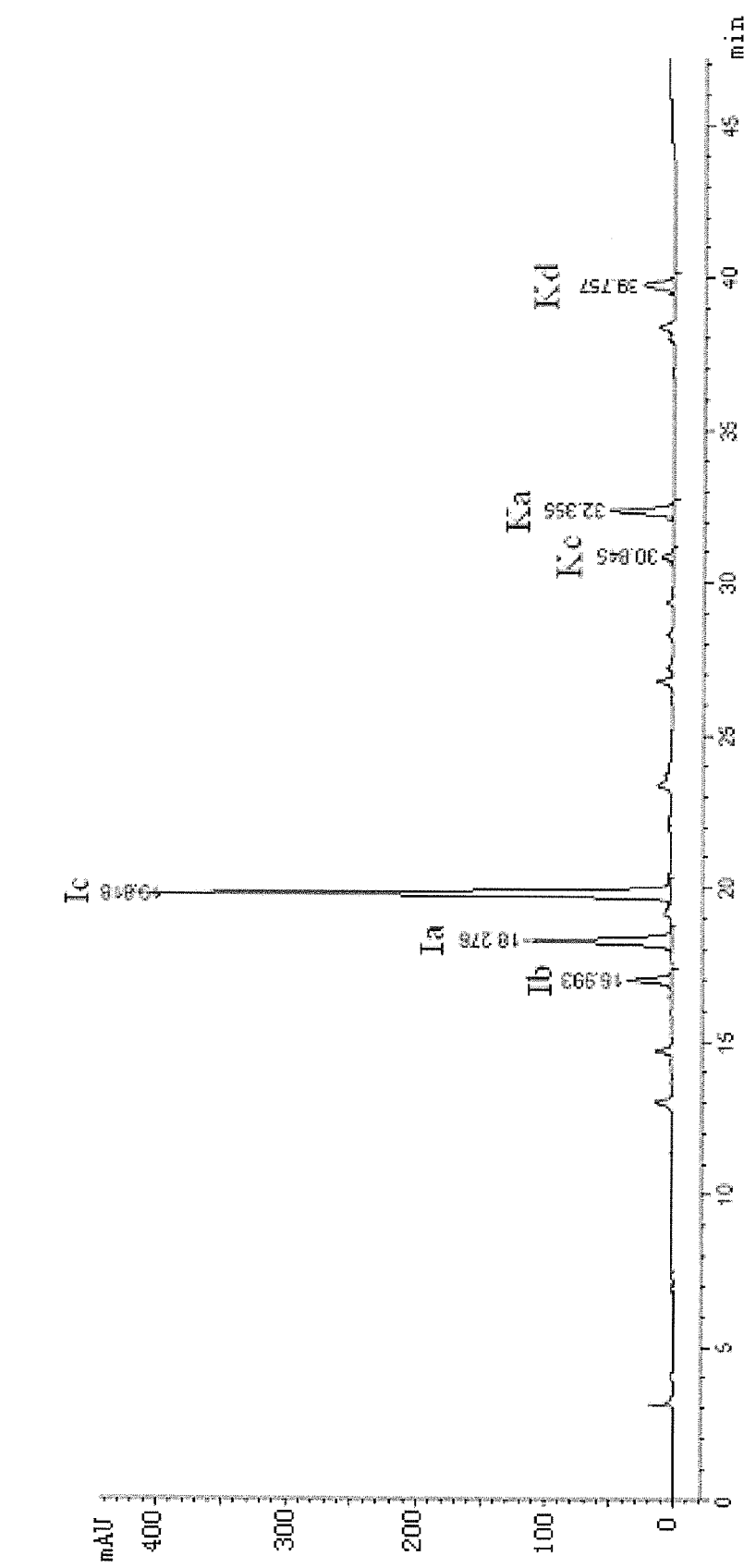
FIG. 4 is a high performance liquid chromatogram of the sample C3 prepared in Comparative Example 3.

FIG. 1 is the chromatogram of sample A1 prepared in Example 1, FIG. 2 is the chromatogram of sample C1 prepared in Comparative Example 1, FIG. 3 is the chromatogram of sample C2 prepared in Comparative Example 2, and FIG. 4 is the chromatogram of sample C3 prepared in Comparative Example 3. In FIGS. 1-4, spectral peaks Kc, Ka and Kd indicate three main saponins of *I. kudingcha* [ilekudinoside C (KDC-C), ilekudinoside A (KDC-A) and ilekudinoside D (KDC-D)] respectively; spectral peaks Ia, Ib and Ic indicate ingredients of three isochlorogenic acids (isochlorogenic acid B, isochlorogenic acid A and isochlorogenic acid C) respectively.

HPLC detection results of samples A1 and A2 prepared in Examples 1 and 2, and samples C1, C2 and C3 prepared in Comparative Examples 1, 2 and 3 were listed in Table 2.

TABLE 2

Content results of saponins and isochlorogenic acids in respective extracts detected by HPLC method

| Sample | extraction yield | Ingredients of *I. kudingcha* saponins/% | | | | Ingredients of isochlorogenic acids/% | | | |
|---|---|---|---|---|---|---|---|---|---|
| | | KDC-C | KDC-A | KDC-D | Total | isoB | isoA | isoC | Total |
| A1 | 13.07% | 4.27 | 19.50 | 4.26 | 28.03 | 0.15 | 0.33 | 0.56 | 1.04 |
| A2 | 10.06% | 4.45 | 20.06 | 4.78 | 29.69 | 0.26 | 0.63 | 1.29 | 2.18 |
| C1 | 30% | 2.15 | 4.82 | 2.50 | 9.47 | 4.24 | 13.31 | 15.50 | 33.05 |
| C2 | 22.05% | 2.68 | 5.90 | 3.19 | 11.77 | 4.02 | 12.51 | 14.52 | 31.04 |
| C3 | 20.56% | 3.21 | 6.59 | 3.37 | 13.17 | 3.16 | 10.87 | 12.92 | 26.95 |

Through comparison of results in FIGS. 1-4 and data in Table 2, it can be seen that ingredients of isocholrogenic acids cannot be removed when water and/or ethanol of low concentration are used, while ingredients of isocholrogenic acids can be removed when alkaline ethanol of low concentration is used to perform the elution, so that extract of *I. kudingcha* with high purity of total saponins can be obtained.

2. Determination of Total Saponins by UV Absorption

About 10 mg extract was accurately weighed (3 batches in all), then introduced into 25 ml volumetric flasks, and diluted with methanol to the volume, then 0.8 ml solution was precisely measured and transferred into a 10 ml glass tube with a plug, evaporated at 80° C. in water bath to dryness, and 3 batches of samples were obtained. Ilekudinoside A (0.535 mg/ml) was used as the standard solution, and 0.1 mL, 0.2 mL and 0.4 mL standard solutions were respectively transferred into 10 ml glass tubes with plugs, and evaporated at 80° C. in water bath to dryness.

0.1 g vanillin was weighed and placed into a 10 ml glass tube with a plug, and 2 ml glacial acetic acid was added to the glass tube, then 8 ml perchloric acid was added to the glass tube after vanillin was dissolved, and then the mixture was shaken up, so that a golden chromogenic agent was obtained.

Then 1 ml chromogenic agent was put into the glass tubes with dried samples and glass tubes with standard samples respectively. The glass tubes were cooled immediately after being heated at 60° C. in water bath for 15 min, then 5 ml glacial acetic acid was added to the above glass tubes before UV adsorption values were detected at 538 nm after the mixtures were shaken up.

Measurement results of the contents of total saponins of samples A1 and A2 prepared in Examples 1 and 2, and samples C1, C2 and C3 prepared in Comparative Examples 1, 2 and 3 are listed in Table 3.

TABLE 3

Results of contents of total saponins in respective extracts by UV method

| Sample | Content of total saponins/% |
|---|---|
| A1 | 88.24 |
| A2 | 86.02 |
| C1 | 53.11 |
| C2 | 65.03 |
| C3 | 68.02 |

By comparing data shown in Table 3, it can be seen that the contents of total saponins of samples A1 and A2 are significantly higher than that of samples C1, C2 and C3, which indicates that the content of total saponins can be significantly increased by removing impurities. However, it has been found that there are some inaccuracies in determining contents by UV method. For example, although the contents of total saponins in samples C2 and C3 determined by the UV method were higher, it was found by HPLC detection that there were still a large amount of isochlorogenic acids in samples C2 and C3. This is because glacial acetic acid-vanillin colorimetry lacks specificity, and many compounds similar to glycosides all have the above color reaction, which results in inaccuracy of the determination results.

Efficacy Test

Following experiments were conducted to test the curative effect of the extract of *I. kudingcha* leaves prepared in Example 1.

ApoE−/− mice were divided into four groups randomly by weight.

(1) Negative control group (CG): mice in this group were fed normally for 7 weeks, and intragastrically administrated with normal saline.

(2) High fat control group (HG): mice in this group were fed with high fat diet containing 0.2% cholesterol for 7 weeks, and intragastrically administrated with normal saline every day simultaneously.

(3) Atorvastatin (Ator) therapeutic group (AG): mice in this group were fed with high fat diet for a week, and then intragastrically administrated with atorvastatin (50 mg/kg/d) every day for 6 weeks, and fed with high fat diet continually at the same time.

(4) *I. kudingcha* total saponin therapeutic group (SG): the course of treatment is similar to that of AG, with the only difference between SG and AG lies in that the dosage of the total saponins from *I. kudingcha* is 300 mg/kg/d.

Figure 5:
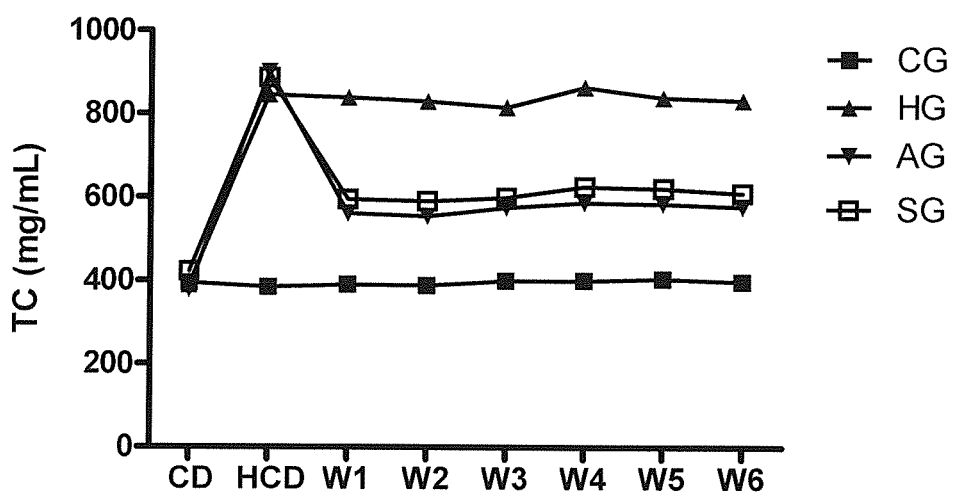
FIG. 5 shows effect of total saponins from *I. kudingcha* on the level of total cholesterol in the plasma of ApoE−/− mice.

1. Effect of Total Saponins from *I. kudingcha* Leaves on the Level of Total Cholesterol (TC) in the Plasma Effect of total saponins from *I. kudingcha* leaves on level of total cholesterol (TC) in the plasma of ApoE−/− mice is shown in FIG. 5. After ApoE−/− mice were fed with high fat diet for one week, the level of TC in the plasma was increased from 300~400 mg/dL to about 800 mg/dL, so that the hypercholesterolemia was formed, and then the mice were intragastrically administrated with drugs. The results indicated that, compared with mice in HG, the levels of plasma TC of mice were reduced in all administration groups. The levels of plasma TC of mice in groups of AG and SG were both reduced by 30%~35%, and the efficacy of the two groups are substantially the same, with no significant difference. The efficacy of drugs lasted 6 weeks and kept stable.

Figure 6:
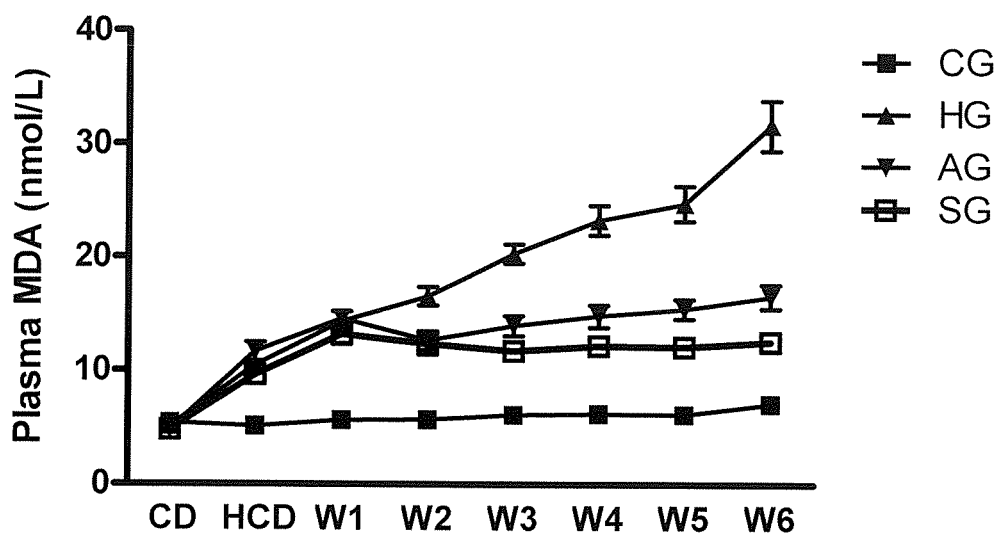
FIG. 6 shows effect of total saponins from *I. kudingcha* on the level of MDA in the plasma of ApoE−/− mice.

2. Effect of Total Saponins from *I. kudingcha* Leaves on Plasma Malondialdehyde (MDA) Levels As shown in FIG. 6, plasma MDA levels of ApoE−/− mice were affected by the total saponins from *I. kudingcha* leaves. As the mice were fed with high fat diet day by day, the plasma MDA level of mice in group HG after six weeks' administration was about five times more than that of mice before administration. Compared with mice in group HG, the increase in plasma MDA levels of mice in groups of AG and SG were significantly inhibited since the second week (W2) of administration, and the efficacy were kept until the end of administration. Plasma MDA levels of mice in group AG began to rise since the fourth week (W4) of administration, and reached 16.5 nmol/L at the sixth week (W6) of administration, which was almost 1.5 times higher than that of mice before administration. However, there was almost no increase in the plasma MDA level of mice in group SG from the beginning of administration to the end of the experiments. The above results indicates that both atorvastatin and saponins from *I. kudingcha* leaves can inhibit oxidation of plasma lipids, and compared with mice in group AG, the increase in plasma MDA levels of mice in group SG was much more efficiently inhibited by the total saponins from *I. kudingcha* leaves since the fifth week (W5) of administration, and the difference in efficacies between the two groups was significant.

3. Effect of Total Saponins from *I. kudingcha* Leaves on Arteriosclerosis

Figure 7:
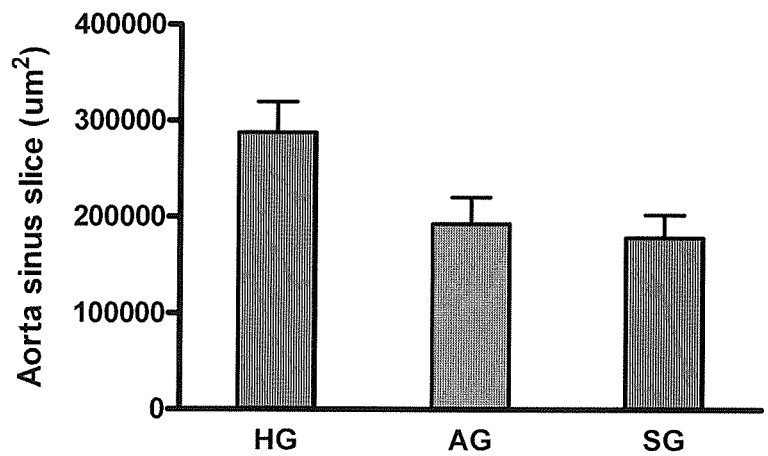
FIG. 7 shows effect of total saponins from *I. kudingcha* on atherosclerosis.

Effect of total saponins from *I. kudingcha* leaves on arteriosclerotic area of ApoE−/− mice aortic outflow tract is shown in FIG. 7. There is significant difference ($p<0.05$) between groups of CG and HG, indicating that the model was successful. Also there are significant differences ($p<0.01$) both between SG and HG and between AG and HG, indicating that both atorvastatin and total saponins from *I. kudingcha* leaves can significantly inhibit the formation of atherosclerotic plaque of aortic outflow tract, with the inhibition rate reaching about 40%.

Figure 8:
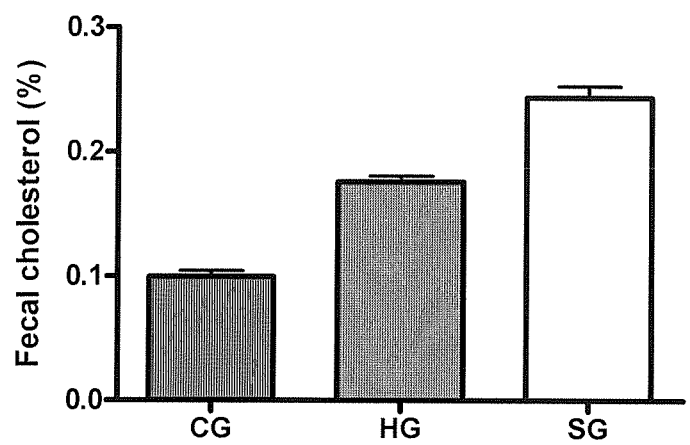
FIG. 8 shows effect of total saponins from *I. kudingcha* on the content of total cholesterol in feces.

4. Effect of Total Saponins from *I. kudingcha* Leaves on the Content of Total Cholesterol in Feces In order to investigate the possible mechanism of reducing plasma cholesterol by the total saponins from *I. kudingcha* leaves, the content of total cholesterol in feces of ApoE−/− mice was determined, so as to determine the effect of drugs on the absorption of cholesterol in the mice. As shown in FIG. 8, there is a significant difference ($^\#P<0.05$) between the groups of SG and CG, and there is also a significant difference ($*P<0.05$) between the groups of SG and HG. The results indicate that the excretion of cholesterol in the mice is increased by 75% after the mice are fed with high-cholesterol diets, and which is significantly different from that of the mice in group CG. Compared with mice in group HG, the excretion of cholesterol in the feces of the mice administrated by SG is increased by about 40%, and difference between these two groups was significant.

Figure 9:
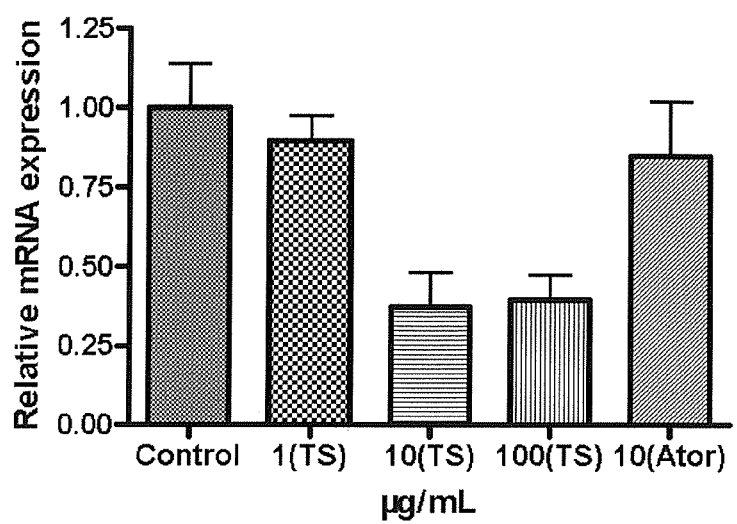
FIG. 9 shows effect of total saponins from *I. kudingcha* on the expression of ACAT2 mRNA in Caco-2 cell.

5. Effect of Total Saponins from *I. kudingcha* Leaves on the Expression of Hepatic ACAT2 mRNA in Caco-2 Cell Previous research showed that the total saponins from *I. kudingcha* leaves could increase the excretion of cholesterol and reduce the content of TC in small intestine, therefore the mRNA expression levels of the related genes were detected. The results indicated that the expression level of mRNA of ACAT2 is affected by the total saponins from *I. kudingcha* leaves, and the result is shown in FIG. 9, in which TS represents the total saponins from *I. kudingcha* and Ator represents atorvastatin. There is a significant difference ($^\#p<0.05$) compared with CG. It can be obtained from the results that the mRNA expression of ACAT2 has been reduced by 50% respectively by total saponins of 10 μg/mL and 100 μg/mL, which is significantly different from that of group CG. However, the total saponins from *I. kudingcha* have no effect on the expression of other screened genes. This investigation indicates that the mechanism of reducing blood lipids by the total saponins from *I. kudingcha* leaves may be that: the total saponins from *I. kudingcha* leaves may reduce blood lipids by inhibiting the activity of ACAT in intestinal tract and liver, thereby the absorption of cholesterol in intestinal tract can be inhibited.

It can be seen from the results of the efficacy detection that the extract from *I. kudingcha* leaves prepared by the present invention has a significant effect on reducing cholesterol and blood lipids and resisting atherosclerosis, with similar effect as drugs of statins.

The invention claimed is:

1. An extraction method for *Ilex kudingcha* C. J. Tseng leaves, comprising the following steps:
   (1) subjecting *I. kudingcha* leaves to refluxing extraction with 50~70 v/v % ethanol aqueous solution to obtain an extract solution;
   (2) filtering the extract solution and removing ethanol from the extract solution;
   (3) adsorbing the solution obtained in step (2) by a macroporous resin column, and eluting the resin column with $H_2O$, 10~30 v/v % alkaline ethanol aqueous solution with pH 9~11, 10~30 v/v % ethanol aqueous solution and 50~70 v/v % ethanol aqueous solution, successively; and
   (4) collecting, concentrating and drying the eluate of 50~70 v/v % ethanol aqueous solution to obtain an extract of *I. kudingcha* leaves.

2. The method according to claim 1, wherein the concentration of the ethanol aqueous solution in step (1) is 55~65 v/v %; and the concentration of the last ethanol aqueous solution in step (3) is 55~65 v/v %.

3. The method according to claim 2, wherein the concentration of the ethanol aqueous solution in step (1) is 60 v/v %; and the concentration of the last ethanol aqueous solution in step (3) is 60 v/v %.

4. The method according to claim 1, wherein in step (1), the extraction is performed 1~8 times, and time for each refluxing extraction is 0.5~5 h.

5. The method according to claim 4, wherein in step (1), the extraction is performed 2~4 times, and time for each refluxing extraction is 0.5~2 h.

6. The method according to claim 1, wherein the removing ethanol is under reduced pressure in step (2); and the concentrating is under reduced pressure, and the drying is vacuum drying in step (4).

7. The method according to claim 1, wherein in step (3), a ratio of diameter to height of the macroporous resin column is 1:3~10, and a weight ratio of macroporous resin and *I. kudingcha* leaves is 5~15:1.

8. The method according to claim 7, wherein in step (3), the ratio of diameter to height of the macroporous resin column is 1:4~7, and the weight ratio of macroporous resin and *I. kudingcha* leaves is 6~10:1.

9. The method according to claim 8, wherein in step (3), the ratio of diameter to height of the macroporous resin column is 1:6.

10. The method according to claim 1, wherein in step (3), the pH of the alkaline ethanol aqueous solution is 10.

11. The method according to claim 1, wherein the method further comprising step (5): combining the eluents of 10~30 v/v % alkaline ethanol aqueous solution (pH 9~11) and 10~30 v/v % ethanol aqueous solution, adjusting pH of the combined solution to pH 2~3, and then concentrating and drying the combined solution to obtain total isochlorogenic acids.

12. The method according to claim 1, wherein the method further comprises: ethanol separated in step (2) and/or ethanol separated in step (4) are recovered to be used in refluxing extraction in step (1) again.

13. The method according to claim 1, wherein the concentration of the ethanol aqueous solution in step (1) is 55~65 v/v %; and the concentration of the last ethanol aqueous solution in step (3) is 55~65 v/v %; and wherein in step (1), the extraction is performed 1~8 times, and time for each refluxing extraction is 0.5~5 h.

14. The method according to claim 13, wherein the removing ethanol is under reduced pressure in step (2); and the concentrating is under reduced pressure, and the drying is vacuum drying in step (4).

15. The method according to claim 14, wherein in step (3), the pH of the alkaline ethanol aqueous solution is 10.

16. The method according to claim 15, wherein the method further comprising step (5): combining the eluents of 10~30 v/v % alkaline ethanol aqueous solution and 10~30 v/v % ethanol aqueous solution, adjusting pH of the combined solution to pH 2~3, and then concentrating and drying the combined solution to obtain total isochlorogenic acids.

17. The method according to claim 15, wherein the method further comprises: ethanol separated in step (2) and/or ethanol separated in step (4) are recovered to be used in refluxing extraction in step (1) again.

18. A method for reducing cholesterol and blood lipids and anti-atherosclerosis by using total saponins extracted from *I. kudingcha* leaves according to claim 1 and comprising less than or equal to 2.18% isochlorogenic acids detected by high performance liquid chromatography.

* * * * *